(12) United States Patent
Crouse et al.

(10) Patent No.: US 9,228,873 B2
(45) Date of Patent: Jan. 5, 2016

(54) FLUID BLOB TRACKING FOR EVALUATION OF MULTIPHASE FLOW SIMULATIONS

(71) Applicant: Exa Corporation, Burlington, MA (US)

(72) Inventors: Bernd Crouse, Berkeley, CA (US); David M. Freed, Brisbane, CA (US); Nils Koliha, San Leandro, CA (US)

(73) Assignee: Exa Corporation, Burlington, MA (US)

( * ) Notice: Subject to any disclaimer, the term of this patent is extended or adjusted under 35 U.S.C. 154(b) by 0 days.

(21) Appl. No.: 14/660,019

(22) Filed: Mar. 17, 2015

(65) Prior Publication Data

US 2015/0268080 A1    Sep. 24, 2015

Related U.S. Application Data

(60) Provisional application No. 61/954,798, filed on Mar. 18, 2014.

(51) Int. Cl.
*G06F 19/00* (2011.01)
*G01F 1/74* (2006.01)

(52) U.S. Cl.
CPC .......................................... *G01F 1/74* (2013.01)

(58) Field of Classification Search
CPC .... E21B 43/24; E21B 43/243; E21B 43/2401
USPC ................................. 702/45, 13, 14, 182–185
See application file for complete search history.

(56) References Cited

U.S. PATENT DOCUMENTS

| | | | |
|---|---|---|---|
| 6,318,156 B1 | 11/2001 | Dutton et al. | |
| 6,928,399 B1 | 8/2005 | Watts, III et al. | |
| 8,583,411 B2 | 11/2013 | Fung | |
| 2007/0016389 A1* | 1/2007 | Ozgen | 703/10 |
| 2014/0019053 A1 | 1/2015 | de Prisco | |
| 2015/0066463 A1* | 3/2015 | Shetty et al. | 703/10 |

OTHER PUBLICATIONS

Yiotis, et al.; "Blob population dynamics during immiscible two-phase flows in reconstructed prorous media"; Physical Review E 87, 033001; 2013; 12 pages.
Hoshen et al.; "Percolation and cluster distribution. I. Cluster multiple labeling technique and critical concentration algorithm"; Physical Review B, vol. 14, No. 8; Oct. 15, 1976; 8 pages.
Catala, G., et al. Fluid Flow Fundamentals. Oilfield Review, Schlumberger. Winter 1996. [Retrieved May 15, 2015]. Retrieved from http://www.slb.com/--/media/Filesfresources/oilfield_review/ors96/win96/12966164.pdf entire document; pp. 61-64.
(Continued)

*Primary Examiner* — Edward Raymond
(74) *Attorney, Agent, or Firm* — Fish & Richardson P.C.

(57) ABSTRACT

Methods, systems, and apparatus, including computer programs encoded on computer storage media, for fluid blob tracking. One of the methods includes identifying, by a computer system, a connected fluid phase region in a flow simulation. The method includes tracking, by the computer system, the connected fluid phase region over a first timeframe and a second timeframe. The method also includes determining, by the computer system, movement of the connected fluid phase region from the first timeframe to the second timeframe based on the tracking.

30 Claims, 5 Drawing Sheets

(56) References Cited

OTHER PUBLICATIONS

Pepiot et al., Numerical analysis of the dynamics of two- and three-dimensional fluidized bed reactors using an Euler-Lagrange approach. Powder Technology 220 (2012) 104-121. (Retrieved May 15, 2015). Retrieved from http://ctflab.mae.cornell.edu/papers/Pepiot.%20Desjardins.%202012.%20Numerical%20analysis%20of%20the%20dynamics%20of%20two-%20and%20three-dim8nsional%20fluidized%20bed%20reactors%20using%20an%20Eul8r-Langrange%20approach.pdf entired ocument; 18 pp.

International Search Report and Written Opinion; PCT/US2015/021075; Ex. Copenheaver; Jul. 8, 2015; 13 pp.

\* cited by examiner

FLUID BLOB TRACKING FOR EVALUATION OF MULTIPHASE FLOW SIMULATIONS

CLAIM OF PRIORITY

This application claims priority under 35 USC §119(e) to U.S. Provisional Patent Application Ser. No. 61/954,798, filed on Mar. 18, 2014 and entitled "FLUID BLOB TRACKING FOR EVALUATION OF MULTIPHASE FLOW SIMULATIONS," the entire contents of which are hereby incorporated by reference.

TECHNICAL FIELD

This specification relates to multi-phase flows.

BACKGROUND

Multi-phase or multi-component (from herein called multiphase) flow is widespread in many engineering disciplines. In some cases, the geometry which defines the boundaries confining the multiphase flow are known precisely, such as a system of pipes or channels. Other scenarios involve highly random and complex geometry, such as the pore space of a porous rock. One example of an application of multiphase flow through a complex porous media is the study of oil and water flow in oil reservoir rock. Another example is oil, water, and gas in reservoir rock. Another example is liquid and gas flow in a porous material acting as a gas diffusion layer in a chemical separation process. A key property of this flow behavior is the "relative permeability" of each fluid phase, which characterizes how easily that phase moves through the rock for the specified conditions. In multiphase flow in porous media, the relative permeability of a phase is a dimensionless measure of the effective permeability of that phase. It is the ratio of the effective permeability of that phase to the absolute permeability.

An especially important aspect of the relative permeability of oil/water flow in porous rock is the behavior at and near the "residual oil saturation". The term saturation refers to the volume fraction of water over total fluid (oil and water), and residual oil saturation refers to the saturation value for which the average oil velocity (and hence the oil relative permeability) is essentially zero. Since for this condition the oil cannot move, the corresponding volume fraction of oil is known as the "residual oil". This is an important quantity because it represents the minimum amount of oil that cannot be extracted from the rock, hence the residual oil saturation value, and the relative permeability as a function of saturation as the saturation approaches the residual oil saturation value, is especially valuable information for determining the value of the reservoir and for assessing potential enhanced oil recovery (EOR) methods.

For multiphase flow measurement or prediction methods, it is therefore important to have a highly accurate method to determine the permeability of the fluid in the porous material even when it is very tiny, since a key goal is to find the saturation value for which it effectively reaches zero.

SUMMARY

In general, one innovative aspect of the subject matter described in this specification can be embodied in methods that include the actions of identifying, by a computer system, a connected fluid phase region in a flow simulation. In aspect 1, the method includes the actions of tracking, by the computer system, the connected fluid phase region over a first timeframe and a second timeframe. The methods includes the actions of determining, by the computer system, movement of the connected fluid phase region from the first timeframe to the second timeframe based on the tracking.

The foregoing and other embodiments can each optionally include one or more of the following features, alone or in combination.

In aspect 2 according to aspect 1, identifying the connected fluid phase region may include identifying a fluid phase region having a first phase, identifying fluid phase regions neighboring the first phase region and having the first phase, and assigning the neighboring fluid phase regions to the connected fluid phase region.

In aspect 3 according to any of aspects 1 and 2, the flow simulation may include a plurality of fluid phase regions, the method may further include identifying a phase for each fluid phase region.

In aspect 4, according to any of aspects 1, 2, and 3, identifying the phase for each fluid phase region may include calculating a ratio of the density of a first phase in the respective region minus the density of all other phases in the respective region to the sum of the density of all of the phases in the respective region, and comparing the ratio to a threshold.

In aspect 5, according to any of aspects 1, 2, 3, and 4, the connected fluid phase region may include oil; and the method may further include determining trapped oil based on the movement.

In aspect 6, accord to any of aspects 1, 2, 3, 4, and 5, tracking the connected fluid phase region may include at least one of: identifying that the connected fluid phase region has moved, identifying that the connected fluid phase region has split into multiple connected fluid phase regions, and identifying that the connected fluid phase region has merged with another connected fluid phase region.

In aspect 7, according to any of aspects 1, 2, 3, 4, 5, and 6, tracking the connected fluid phase region over a series of timeframes may include identifying a first connected fluid phase region in a first timeframe, and identifying a second connected fluid phase region in a second timeframe as being the first connected fluid phase region based on a spatial proximity between the first connected fluid phase region and the second connected fluid phase region.

In aspect 8, according to any of aspects 1, 2, 3, 4, 5, 6, and 7, the spatial proximity may include an overlap of fluid phase regions between the first connected fluid phase region and the second connected fluid phase region.

In aspect 9, according to any of aspects 1, 2, 3, 4, 5, 6, 7, and 8, determining the movement of the connected fluid phase region may include calculating a center of gravity for the connected fluid phase region, and determining a velocity for the connected fluid phase region based on the center of gravity.

In aspect 10, according to any of aspects 1, 2, 3, 4, 5, 6, 7, 8, and 9, determining the velocity of the connected fluid phase region may further include identifying the change in the center of gravity for the connected fluid phase region between the first timeframe and the second timeframe.

In aspect 11, according to any of aspects 1, 2, 3, 4, 5, 6, 7, 8, 9, and 10, the connected fluid phase region may include a series of volume elements, each volume element having the same phase and may be in contact with at least one other volume element in the series.

In aspect 12, according to any of aspects 1, 2, 3, 4, 5, 6, 7, 8, 9, 10, and 11, the method may further include identifying a plurality of connected fluid phase regions, each connected fluid phase region having a target phase, determining a velocity for each connected fluid phase region in the plurality of connected fluid phase regions, and assigning an permeability to the target phase based on the velocity of each connected fluid phase region in the plurality of connected fluid phase regions.

In aspect 13, according to any of aspects 1, 2, 3, 4, 5, 6, 7, 8, 9, 10, 11, and 12, assigning the permeability to the phase may include calculating a weighted average of the velocity of each connected fluid phase region having the target phase.

In aspect 14, according to any of aspects 1, 2, 3, 4, 5, 6, 7, 8, 9, 10, 11, 12, and 13, the velocities may be weighted based on the volumes of the connected fluid phase regions.

In aspect 15, according to any of aspects 1, 2, 3, 4, 5, 6, 7, 8, 9, 10, 11, 12, 13, and 14, the method may further include determining properties of the connected fluid phase region in the first timeframe and the second timeframe.

In aspect 16, according to any of aspects 1, 2, 3, 4, 5, 6, 7, 8, 9, 10, 11, 12, 13, 14, and 15 the properties maybe selected from the group consisting of: volume, effective permeability, and flow rate.

Other embodiments of this aspect include corresponding computer systems, apparatus, and computer programs recorded on one or more computer storage devices, each configured to perform the actions of the methods. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

The embodiments described below can provide one or more of the following advantages. The average velocity of a fluid phase can be determined more accurately when it's very small. As a result of that, the conditions for which a fluid phase average velocity becomes effectively zero can be more accurately determined. Insights into flow behavior may be obtained, for example, how some blobs become trapped, and which blobs contribute to the overall fluid phase permeability. By identifying the blobs that contribute most to the permeability, various simulation modeling processes can be targeted more precisely to achieve the desired effect. Insight can be provided that informs decisions about how to modify the relative permeability vs. saturation curve.

DESCRIPTION

High fidelity computer simulation of flow in porous rock has recently become feasible due to advances in imaging, numerical methods, and high performance computing. The ability to perform multiphase flow simulations in order to accurately predict relative permeability for a reservoir rock sample is an active area of research and commercial interest. One approach of interest involves a digital representation of 3D imaging of porous rock. Image analysis of the digital representation can determine the geometry of the pore space. A numerical multiphase flow simulation for various saturation values can be performed to obtain predictions of flow behavior, including relative permeability as a function of saturation. The flow simulation results can also be used to understand the details of the pore-scale multiphase flow dynamics, which can provide insight suggesting approaches for how to modify the relative permeability vs. saturation curve.

During or at completion of the computer simulation of the multiphase flow, determining the resulting permeability of each fluid phase (e.g. oil, water) can include determining the average velocity of that phase, where phase refers to a region of fluid which has uniform composition and properties and is physically distinct from the other phases, average is taken to mean the spatial average over the entire simulation domain, and velocity is taken to mean the velocity component in a direction of interest. Using a volume integration approach, the average velocity of one fluid phase from the simulation results can be calculated by taking the average of the velocity for all simulation grid cells containing that phase (i.e., sum the fluid velocity over all cells containing that phase and divide by the number of cells).

The volume integration approach can be inaccurate when the average velocity of the fluid phase is very small (close to zero). For example, the volume integration approach can be inaccurate when the signal to noise ratio for the quantity is order unity or lower or the signal is less than twice the noise, where the signal is the correct value and the noise is anything that causes error or uncertainty. When the signal is comparable or lower than the noise then the errors/uncertainties interfere with the determination of the correct values. In this example, the signal is the average fluid phase velocity and the noise includes all sources or errors or uncertainty in measuring that velocity, in particular, spurious velocities.

In some scenarios, these can be non-physical, numerically induced velocities that average out to zero globally but locally are non-zero. The range of magnitude of spurious velocities varies with the details of the numerical scheme. In one example, for capillary number $Ca<1e^{-3}$, the average fluid phase velocity may be low enough to be comparable to the spurious velocities arising from the numerical scheme. A capillary number is a dimensionless number that characterizes the ratio of viscous forces to surface or interfacial tension forces between a liquid and a gas, or between two immiscible liquids, typically given by $$Ca = \frac{\mu u}{\sigma}$$

Where $\mu$ is a dynamic viscosity, u is a characteristic velocity, and $\sigma$ is a surface or interfacial tension.

As such, the volume integration approach can be inaccurate, for example, in measuring the velocity of an oil phase when the saturation is at or near the residual oil saturation. For example, the local (cell-wise) velocities within a connected fluid phase region (i.e. a fluid "blob") can be significantly non-zero even when the region as a whole is not moving. (Here a connected region means that each cell shares a face or a corner with at least one other cell in the region.) These significantly non-zero velocities can occur, for example, due to both physical and numerical reasons; when numerically induced, the non-zero velocities are referred to as spurious velocities. Moreover, while the local velocities within a nonmoving blob should physically sum up to zero, there can be numerical integration effects leading to a small residual non-zero velocity when the volume integration approach is used. This small residual velocity can be caused by finite grid resolution effects and can interfere with the volume integration result for a small average velocity. The impact of these residual effects on the overall simulation accuracy may be negligible, such that the fluid behavior (for example, the actual movement of the phases and their interfacial boundaries) remain highly accurate. (In this context, a small average velocity is observed to be on the order of two orders of magnitude smaller than the maximum local velocities).

Systems and methods for using the results of a computer simulation of multiphase flow to identify and track the motion (flow) of connected fluid phase regions (referred to herein as "blobs"), thereby enabling access to fluid properties and information on a per blob basis, are disclosed herein. The blobs represent physically meaningful fluid structures, such as a single droplet of oil surrounded by water, a connected patch of oil bounded by its interface with water, or a connected patch of oil bounded at some locations by its interface with water and at other locations by a solid boundary. As noted above, the blobs are a connected region where each cell in the blob shares a face or a corner with at least one other cell in the region. Other types of fluids can form the connected fluid phase regions which can be identified and tracked using the methods described herein. By identifying blobs and determining their properties at a certain simulation timeframe, and also tracking them over a series of timeframes, information can be gleaned about the motion and time-varying behavior of each blob and its properties. Analyses of the behavior and properties of each separate blob can be interesting; for example, some blobs of a fluid phase might be stationary while others are moving and therefore contributing to the average velocity of that phase. In that case, it could be useful to examine why some blobs are moving and some are not.

Moreover, tracking the time-varying motion of the blobs of a fluid phase can provide another way for the simulation system to determine the average velocity of that phase. The procedure can include determining the center of gravity (COG) of each blob as a function of time (where COG is the location determined by taking the spatial average of the cell center for all cells belonging to the blob), calculating each blob's velocity from the change in its COG (i.e. distance traveled) per unit time, and calculating the average velocity of the phase as the volume-weighted average of the velocities of the blobs making up that phase. Calculating the average velocity of the phase based on the change in COG for the blobs associated with that phase in the system can provide various advantages. For example, the average velocity calculated this way is not impacted by the numerical integration effects discussed previously even when the average velocity value is small (as defined above), therefore the COG method can be more accurate than the volume integration method under these circumstances. This additional accuracy for average velocity of a fluid phase can have a substantially favorable impact on the analysis of numerical simulation results (for example in predicting the residual oil saturation and the average oil velocity and permeability for saturations near/at the residual oil saturation).

Figure 1:
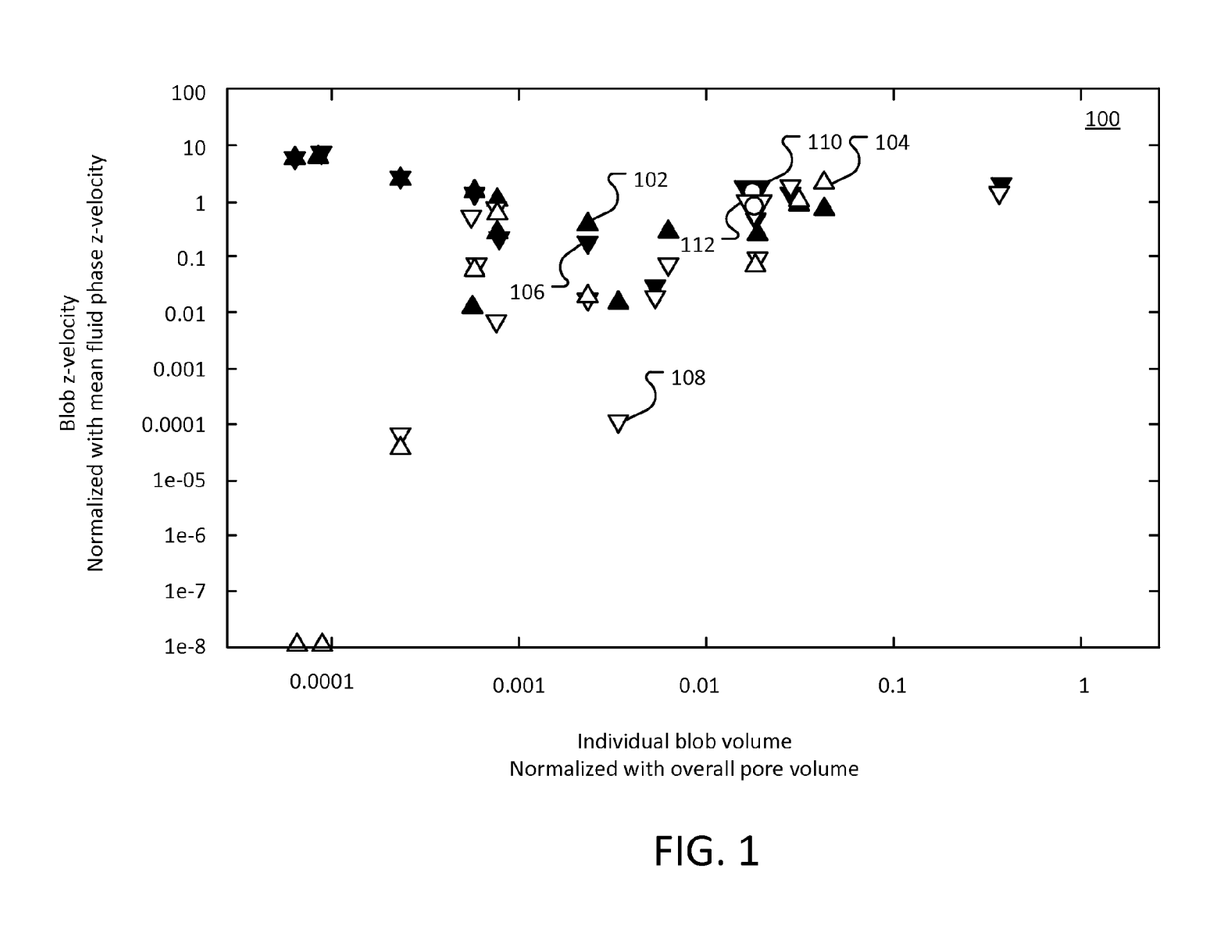
FIG. 1 is a chart of an example simulation that provides a correlation of blob velocities with blob volumes for a benchmark simulation.

FIG. 1 is a chart 100 of results from a benchmark simulation. The chart 100 illustrates the correlation of blob velocities with size for timeframe 14 of the benchmark simulation. Solid black triangles (for example, triangle 102) represent results determined using the volume integrated value while white triangles (for example, triangle 104) represent the values with the COG approach. Triangles pointing up (for example, triangles 102, 104) indicate positive values and triangles pointing down (for example, triangles 106, 108) indicate negative values. Big triangles with an interior circle point are the averages among all blobs. The solid black triangle with the white circle 110 indicates the average among all blobs using the volume integrated approach. The white triangle with the white circle 112 indicates the average value using the COG approach. Note that the black and white triangles are closer together (along a vertical axis) for bigger blobs.

Figure 2:
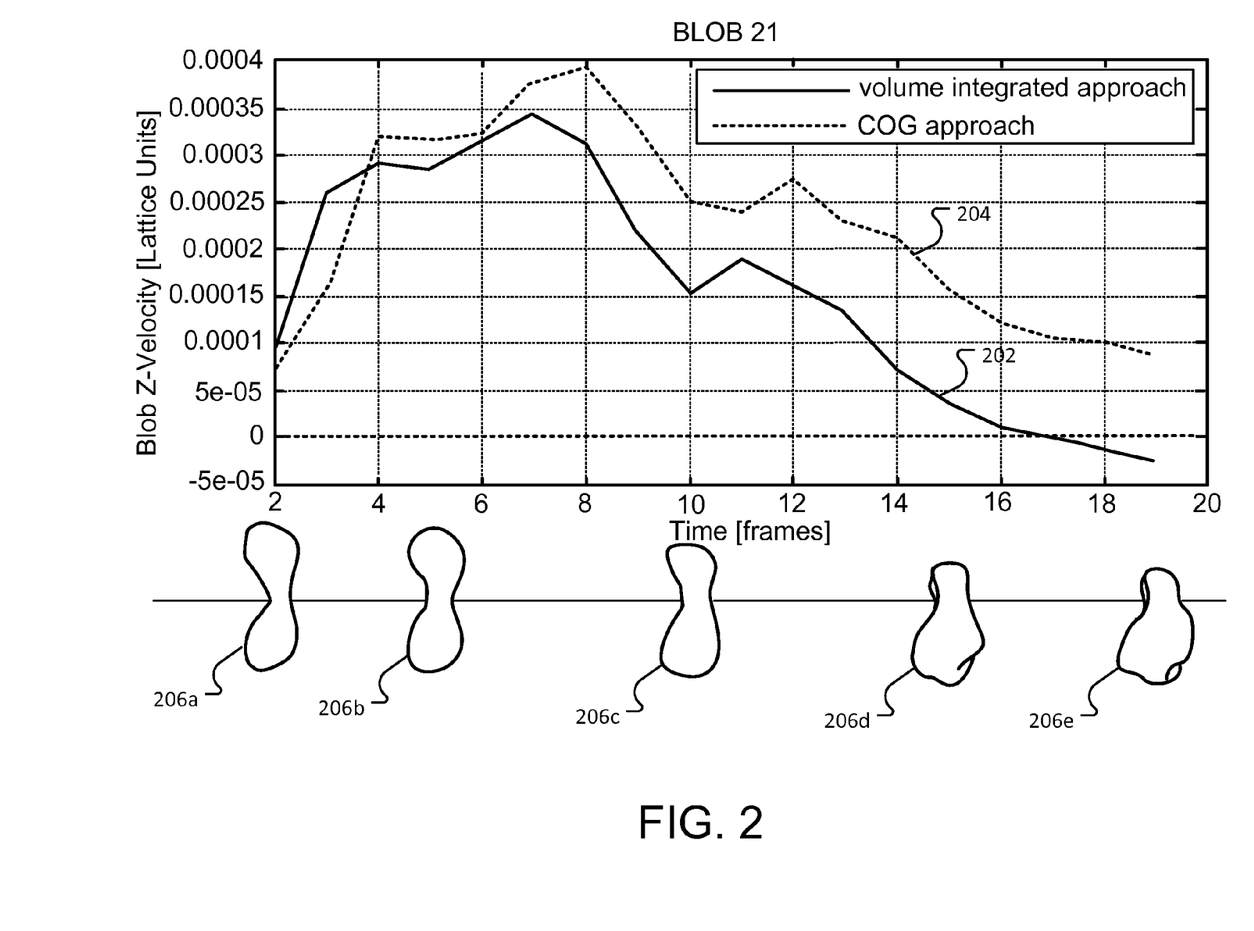
FIG. 2 is a chart of blob z-velocity plotted over time.

FIG. 2 is a chart of blob z-velocity plotted over time. The sold line 202 is obtained with the volume integrated approach while the dashed line 204 is obtained with the COG approach. The gray blob 206a-e deforms over time and is shown below the timeline (z axis vertical, pointing down). Note that the velocity discrepancy is especially severe at the end of the simulation and is of the same order of magnitude as the velocity of the blob.

To reiterate, in some implementations, the Fluid Blob Tracking (FBT) process can include: (1) identification of blobs for each timeframe (instance in time); (2) tracking the blobs over time (from timeframe to timeframe); (3) evaluation of blob-based behavior and statistics to derive integral quantities of interest (e.g. average velocity of a fluid phase). The latter has the advantage of providing a highly accurate method for determining even small average velocity values of a fluid phase even in the presence of significant local spurious velocities that interfere with the volume integration method. The FBT may also provide useful insights about the flow behavior through detailed understanding of the time-varying behavior of the individual fluid structures (blobs).

Blob Identification:

Various methods can be used to identify the connected fluid phase regions (e.g., the blobs). In a numerical simulation system, the numerical simulation domain is divided into a finite number of fluid volumes or "cells". Blob identification for a target phase 1 (e.g. oil in an oil/water mixture) requires first identifying which cells contain that phase.

One way to determine the phase of a cell uses the functions $$A = \frac{\rho_1 - \rho_2}{\rho_1 + \rho_2}$$

where, A is the Atwood number, $\rho_1$ is the density of phase 1, $\rho_2$ is the density of phase 2. The calculated Atwood number of the cell is compared to a threshold value. If the Atwood number for a cell is above the threshold, the cell is qualified as belonging to phase 1, otherwise the cell is qualified as belonging to phase 2. The phase of the cell is stored in a 'state matrix' for every cell of the fluid domain. In some implementations, the threshold may be 0. In one implementation, the phase of each cell is determined by iterating over all the cells and assigning them a true/false value that indicates if the cell belongs to phase 1 based on their calculated Atwood number.

An iteration loop can be used to traverse the state matrix. If a cell that qualifies as being part of phase 1 is encountered during this loop (for example, the calculated Atwood number for that cell is more than the threshold), a filling algorithm is used to create a list of all phase 1 cells that are connected to the initial cell. The filling algorithm iteratively uses a six point nearest-neighbor stencil to examine each cell enclosing the current cell and adds it to the list if its state matrix value is true (that is, the cell qualifies as being part of phase 1). Other filling algorithms can also be used.

This process of examining and adding neighbor cells and then moving to the next member of the list is continued until the list is exhausted, at which point all connected cells of the current blob have been found. This process is continued until all cells in the domain which qualify as Phase 1 belong to a blob of connected cells. Once the complete set of blobs for the given phase is established, each blob's total volume, COG location, and other desired properties are found by examining the properties of its cells. For example, the properties of the blob can include the subdomain occupied by the blob, the extent of the blob in a direction of interest, and the volume-integrated blob velocity. This is achieved by an averaging algorithm that iterates over all the cells of a given blob, sums up the cell property values (optionally weighted by volume of the phase in the cell and/or Atwood number), and divides the sum by the blob volume. The use of cell volume and Atwood number as weighting functions is helpful for the treatment of "interface cells" which may contain significant amounts of each fluid phase; this is found to be important, for example, to accurately determine a blob's COG location and thereby its motion.

When periodic boundary conditions are used across the main flow direction of the simulation domain, blobs crossing one boundary are continued on the opposite end of the domain. For such blobs, the spatial average of the cell centers no longer gives the correct COG. A "blob fusing" step is used to reconnect blobs that have been identified separately but share the same boundary voxels on opposite sides. Blob fusing also allows the identification and recognition of blobs that fully span the domain in the flow direction, with one end of the blob connecting to the other end, such that the blob is effectively continuous (referred to as a channel flow blob). For such blobs, the volume integration approach is used to find the average velocity instead of the approach based on COG, since the fluid in a channel flow blob may be moving even if its COG remains unchanged (while for the remaining blobs the COG average velocity method is still used). This is justified because channel flow blobs typically have relatively large average velocities for which the volume integration method is sufficiently accurate. Moreover, the volume integration approach is used instead of the COG method for a given blob at a given point in time if that blob is a channel flow blob at either the current or the previous point in time, since the COG average velocity is obtained with a backwards oriented finite difference scheme of first order which requires consistently obtained values for both the current and previous time points.

Blob Tracking:

The set of identified connected fluid phase regions (i.e., blobs) can be tracked using various methods. In one example, a set of blobs is identified at time instance x and another set is identified at a later time instance y, and the blobs are tracked by comparing the two sets and matching the blobs from time x to those at time y. The blob matching is based on the degree of spatial overlap between a blob at time x and a blob at time y. A blob at time y is matched to the one at time x with which it has the highest degree of spatial overlap; it is then assigned the same unique identifier (ID) as the blob at time x and inherits that blob's history. The success of this particular overlap matching approach requires that a blob's velocity is less than a critical value defined as the ratio of the blob's characteristic radius over the time difference between times x and y. If needed, a more precise matching algorithm could be used; for example, the COG and velocity of a blob at time x could be used to estimate its COG at time y, and then the difference between estimated and actual COG at time y can be compared to a threshold value to determine whether there is a match. Using this process, the entire history of each blob can be tracked, retrieved, and used to deduce flow information.

The blob matching algorithm can be based on a set of two blob ID matrices, one representing the current time (time y) and one representing the previous time (time x). These matrices store the blob ID for each qualifying cell in the fluid domain, and for each time, each blob has a list of which cells belong to it. This information is used to distinguish three types blob tracking events:

(i) Identity event: A single blob at time y overlaps with one blob at time x; the blob at time y is assigned the ID of the blob at time x.
(ii) Split event: Multiple blobs at time y overlap with one blob at time x; the time y blob that has the biggest volume overlap with the time x blob is assigned the ID of that blob. All other time y blobs that overlapped with the time x blob are assumed to have split off from it and are identified as new blobs created at time instance y (and each is assigned a new unique ID). The time x blob is considered to have lost those blobs that split off from it.
(iii) Merge event: A single blob at time y overlaps with multiple blobs at time x; the time y blob is assigned the ID of the time x blob with which it has the biggest volume overlap. All the other time x overlapping blobs are considered to have been swallowed by the time y blob.

Blob-Based Analyses:

As previously discussed, the blob COG method for determining the average velocity of a fluid phase is highly accurate and overcomes the problem of numerical integration effects that can occur when the local cell velocities are much larger than the average velocity. Since this method is accurate even at the limit of vanishing average velocity values, it enables accurate determination of the multiphase flow relative permeabilities (because relative permeability is proportional to average velocity) across the entire range of saturation values, even those for which a fluid phase's relative permeability is very close to zero. In multiphase flow of oil and water, the oil relative permeability is effectively zero at the residual oil saturation and the water relative permeability is effectively zero at the irreducible water saturation (i.e. the saturation at which all the remaining water in the pore space is trapped and does not move). Furthermore, statistics of blob properties can provide deeper understanding of the pore scale multiphase fluid dynamics; for example, it has been observed over a set of simulation results that there is a correlation between the relative permeability of a fluid phase and its average blob size. In another example, it has been observed that the formation of a flow channel blob dramatically increases relative permeability, and likewise, changes a condition (such as saturation value) in a way that breaking a flow channel blob causes a large decrease in relative permeability.

Given the potential for computer simulation predictions of relative permeability to have lower cost and take less time than the corresponding physical testing process, a multiphase porous media flow simulation method employing the fluid blob tracking invention described herein is expected to have value to the petroleum exploration and production industry.

Output Generation:

Post processing of the blob tracking analysis can be divided into general, per time, and per blob information.

General information can include the total blob volume, total blob velocity in the mean flow direction, and effective and relative permeabilities plotted over time. These plots can be utilized to judge the convergence of the simulation or to identify significant events in the development of the flow.

Per time information can include data plotted for a given moment in time. Among the produced information is a histogram that shows how many blobs are within certain volume ranges. This plot can be used to investigate the size distribution of blobs. Another example of per time data is a correlation plot of COG average velocity and volume integrated average velocity. Each blob present at the considered point in time produces a data point in this plot. A plot showing the correlation of blob size with blob velocity is used in an effort to find a size limit at which blobs are more likely to get trapped or to visualize the size dependent discrepancy of COG average velocity and volume integrated average velocity. FIG. 1 is an example of such a plot.

Per blob plots can be created for focus blobs that are of specific interest. The list of focus blobs can consist of the biggest blobs, the fastest blobs, or the blobs with the highest velocity times volume average. The latter blobs are the ones with the highest impact on permeability. Per blob plots show a blob's volume change in time (e.g., due to merge/loose events), compare the evolution of its COG average velocity and volume integrated average velocity (see FIG. 2), and correlate the COG average velocity and volume integrated average velocity values for each frame that the blob existed.

EXAMPLE

Figure 3:
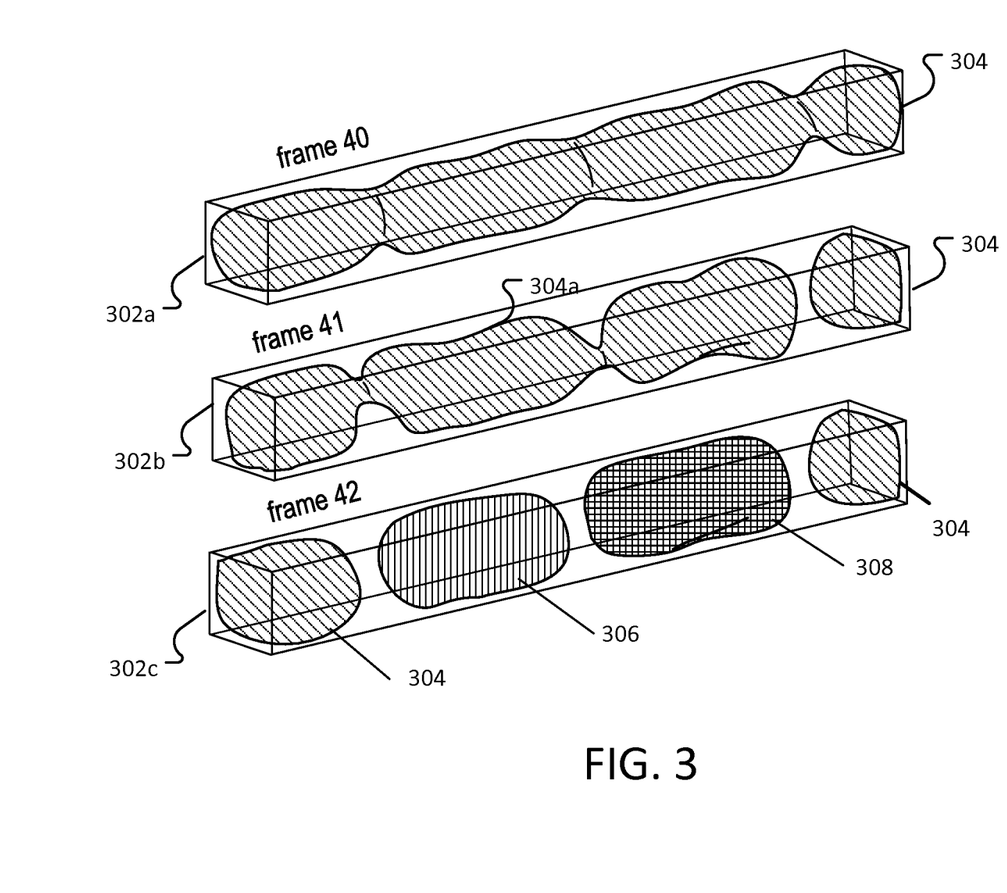
FIG. 3 illustrates an example of the Fluid Blob Tracker applied to a square duct flow with oil and water.

FIG. 3 illustrates an example of the Fluid Blob Tracker applied to a square duct 302a-c flow with oil and water, where three individual blobs form from a single blob with channel flow characteristics. The square duct 302a represents the square duct in frame 40, the square duct 302b represents the square duct at frame 41, and the square duct 302c represents the square duct at frame 42. During the simulation time, oil is replaced by water using Exa's Mass Sink/Source (MSS) concept to model a mass exchange in a periodic environment, therefore, a change in flow topology occurs and will be described below. The entire time line spans over 200 timeframes. At frame 40, the single blob 304 is present in the square duct 302. A split occurs at frame 42 and new blobs are introduced. The blobs are labeled according to their respective ID: a first blob 304 is labeled with ID 0, a second blob 308 with ID 1, and a third blob 306 with ID 2. An excerpt of the summary file shows some of the quantities obtained with blob tracking

| Blob ID | Average Volume | looped | Life | age | Split/merge/loose |
|---|---|---|---|---|---|
| 0 (blob 304) | 21482 | Yes | [0:198] | 199 | L_1_ @42 L_2_ @_42 |
| 1 (blob 308) | 11060 | No | [42:198] | 157 | S_0_@_42 |
| 2 (blob 306) | 10460 | No | [42:198] | 157 | S_0_@_42 | where the blob ID is the blob ID assigned as described above, the average volume identifies the size of each respective blob, and life indicates the frames during which the blob exists in the simulations (for example, blob 302 is present for the entire simulation while blob 308 and blob 306 were created in frame 42). The last column specifies that blob 308 and blob 306 split from blob 302 at frame 42 and that blob 302 lost blob 308 and blob 306 at frame 42. Note that blob 0 extends from one end of the periodically connected fluid domain to the other as indicated by the looped column having a value of 'Yes'.

Figure 4:
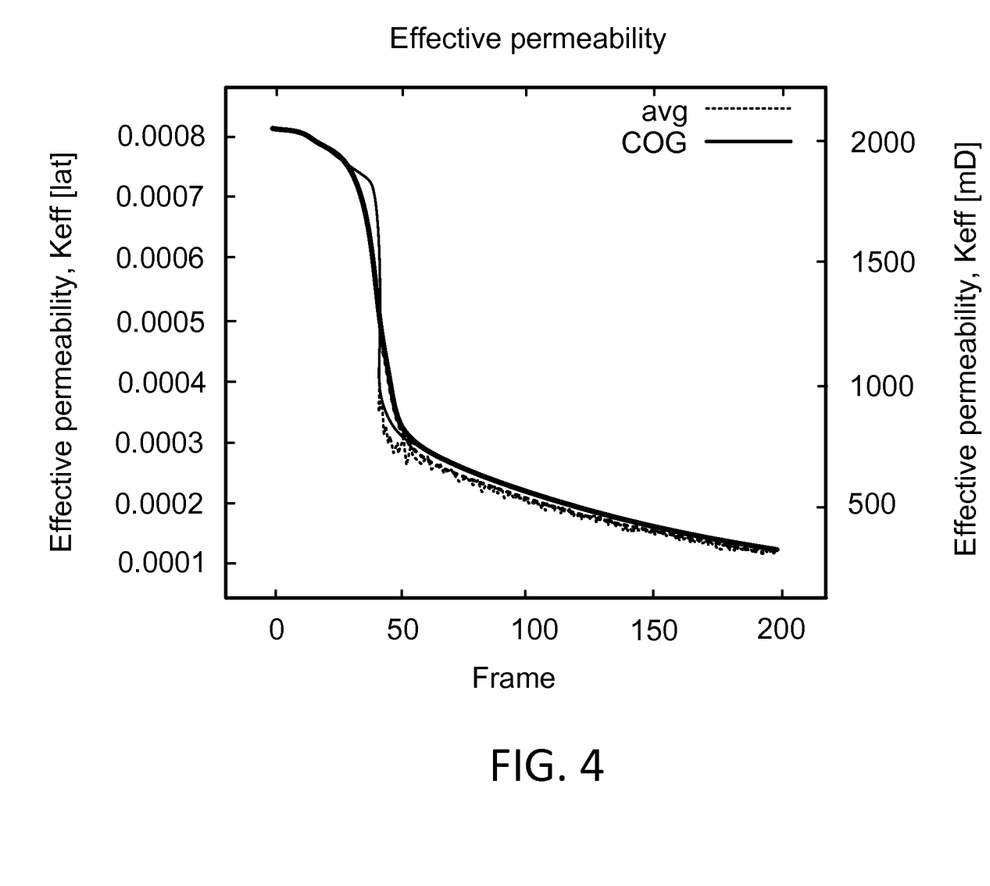
FIG. 4 is a chart plotting the target species' effective permeability over time.

FIG. 4 is a chart plotting the target species' effective permeability over time. Note that the COG derived velocity results in a slightly different effective permeability (solid line) compared to the one derived from the fluid velocity field (dotted line). At very low velocity values, this difference can be substantial.

Figure 5:
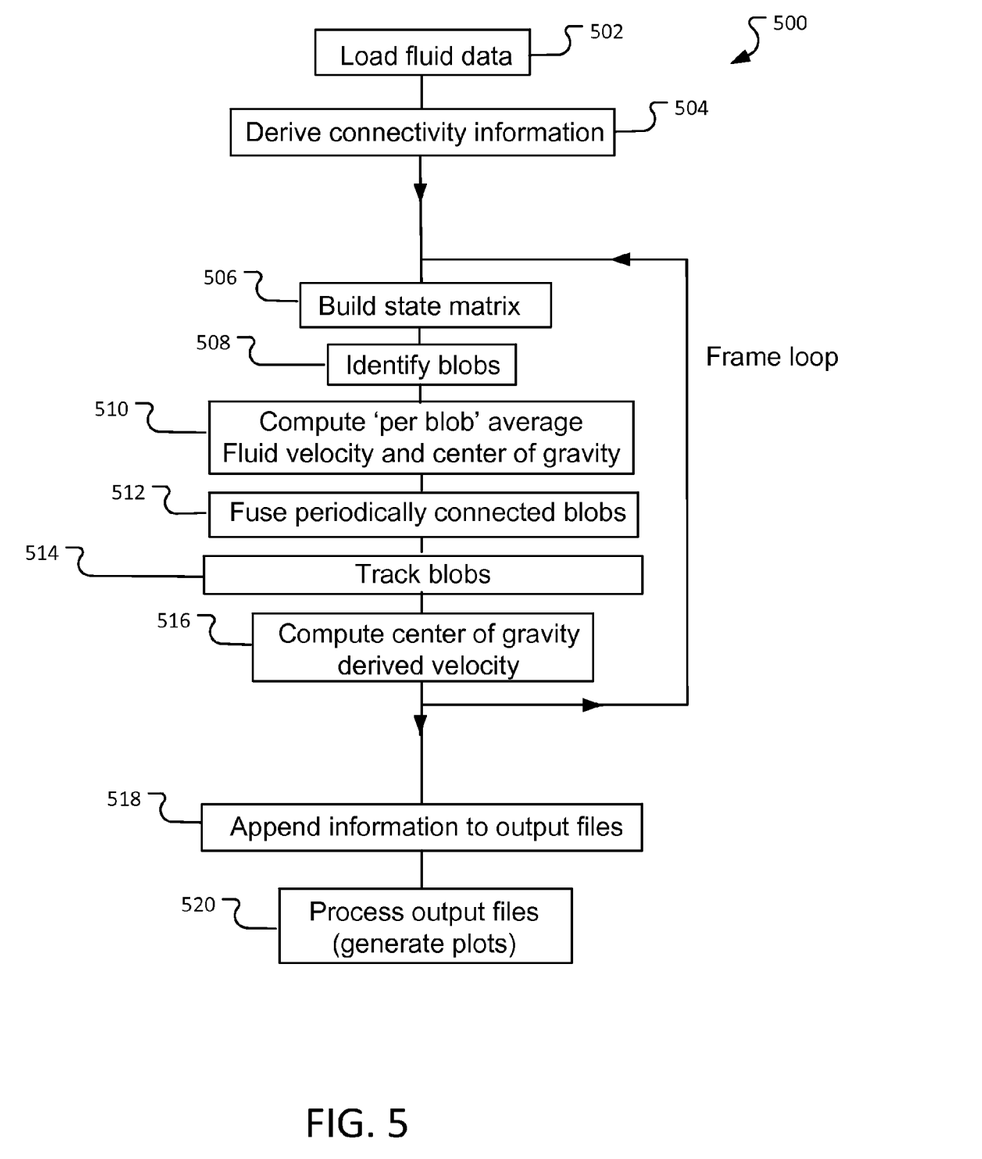
FIG. 5 illustrates an exemplary process 500 for the evaluation of multiphase flow simulations.

FIG. 5 illustrates an exemplary process 500 for the evaluation of multiphase flow simulations. The process can be performed by one or more computer systems including memory and processors. The process can be performed synchronously or in parallel.

Fluid data is loaded (502), for example, from results of a simulation of flow through a digital representation based on 3D imaging of porous rock.

Connectivity information is derived (504). Connectivity information can be derived from an analysis of the digital representation which determines the geometry of the porous space. A flow simulation can be performed. In some implementations, for each voxel within a lattice grid, there is a density for each phase (e.g., a density for water and a density for oil).

A state matrix is built (506). The state matrix identifies which cells in the simulation are identified as being part of which phase. Identifying the phase of the cell in the matrix can include comparing the density of the phases in the voxel. For example, if a cell is mostly water but contains a little oil, then the density of the water in the cell will be much higher than the density of the oil. An Atwood number can be calculated for each voxel. The Atwood number can be used to determine a weighting of how much of each phase is present in the voxel.

Blobs are identified (508). Blobs are made up of voxels that include the target phase and are in contact on at least one side. Blobs can be identified by employing a filling algorithm on voxels that are identified as including the target phase.

"Per blob" average fluid velocity and center of gravity is computed (510). The average fluid velocity and center of gravity can be calculated as described above.

Periodically connected blobs are fused (512). Blobs that exist across periodic boundary conditions can be identified and fused together.

Blobs are tracked (514). As described above, the position of the blobs are tracked over time. Tracking can include identifying that a blob moved between periodic snapshots, divided into multiple blobs, or combined to form a single blob.

Center of gravity and derived velocity is computed (516). The center of gravity can be identified as described above. Changes in the center of gravity over time can be used to derive the velocity of the blob.

Information is appended to output files (518). As information is processed during the simulation, the information is added to output files. The information can include, for example, blob identification numbers, blob velocities, blob volume, blob age, blob split and merge events, and other characteristics.

Output files are processed (520). The output files can be processed to generate graphical output (for example, the charts shown in FIGS. 1, 2, and 4).

The process described above can be used, for example, to determine whether oil is trapped. Trapped oil may refer to oil in pore spaces that cannot be moved because of capillary forces.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs (i.e., one or more modules of computer program instructions, encoded on computer storage medium for execution by, or to control the operation of, data processing apparatus). A computer storage medium can be, or be included in, a computer-readable storage device, a computer-readable storage substrate, a random or serial access memory array or device, or a combination of one or more of them. The computer storage medium can also be, or be included in, one or more separate physical components or media (e.g., multiple CDs, disks, or other storage devices). The subject matter may be implemented on computer program instructions stored on a non-transitory computer storage medium.

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example: a programmable processor, a computer, a system on a chip, or multiple ones, or combinations, of the foregoing. The apparatus can include special purpose logic circuitry (e.g., an FPGA (field programmable gate array) or an ASIC (application specific integrated circuit)). The apparatus can also include, in addition to hardware, code that creates an execution environment for the computer program in question (e.g., code that constitutes processor firmware, a protocol stack, a database management system, an operating system, a cross-platform runtime environment, a virtual machine, or a combination of one or more of them). The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry (e.g., an FPGA (field programmable gate array) or an ASIC (application specific integrated circuit)).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data (e.g., magnetic, magneto optical disks, or optical disks), however, a computer need not have such devices. Moreover, a computer can be embedded in another device (e.g., a mobile telephone, a personal digital assistant (PDA), a mobile audio or video player, a game console, a Global Positioning System (GPS) receiver, or a portable storage device (e.g., a universal serial bus (USB) flash drive)). Devices suitable for storing computer program instructions and data include all forms of non-volatile memory, media and memory devices, including by way of example, semiconductor memory devices (e.g., EPROM, EEPROM, and flash memory devices), magnetic disks (e.g., internal hard disks or removable disks), magneto optical disks, and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback) and input from the user can be received in any form, including acoustic, speech, or tactile input. In addition, a computer can interact with a user by sending documents to and receiving documents from a device that is used by the user (for example, by sending web pages to a web browser on a user's user device in response to requests received from the web browser).

Embodiments of the subject matter described in this specification can be implemented in a computing system that includes a back end component (e.g., as a data server), or that includes a middleware component (e.g., an application server), or that includes a front end component (e.g., a user computer having a graphical user interface or a Web browser through which a user can interact with an implementation of the subject matter described in this specification), or any combination of one or more such back end, middleware, or front end components. The components of the system can be interconnected by any form or medium of digital data communication (e.g., a communication network). Examples of communication networks include a local area network ("LAN") and a wide area network ("WAN"), an inter-network (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method comprising:
   identifying, by a computer system, a connected fluid phase region in a flow simulation;
   tracking, by the computer system, the connected fluid phase region over a first timeframe and a second timeframe; and
   determining, by the computer system, movement of the connected fluid phase region from the first timeframe to the second timeframe based on the tracking.

2. The computer-implemented method of claim 1, wherein identifying the connected fluid phase region comprises:
   identifying a fluid phase region having a first phase;
   identifying fluid phase regions neighboring the first phase region and having the first phase; and
   assigning the neighboring fluid phase regions to the connected fluid phase region.

3. The computer-implemented method of claim 1, wherein the flow simulation comprises a plurality of fluid phase regions; and
   the method further comprises identifying a phase for each fluid phase region.

4. The computer-implemented method of claim 3, wherein identifying the phase for each fluid phase region comprises:
   calculating a ratio of the density of a first phase in the respective region minus the density of all other phases in the respective region to the sum of the density of all of the phases in the respective region; and
   comparing the ratio to a threshold.

5. The computer-implemented method of claim 1, wherein the connected fluid phase region comprises oil; and
   the method further comprises determining trapped oil based on the movement.

6. The computer-implemented method of claim 1, wherein tracking the connected fluid phase region comprises at least one of: identifying that the connected fluid phase region has moved, identifying that the connected fluid phase region has split into multiple connected fluid phase regions, and identifying that the connected fluid phase region has merged with another connected fluid phase region.

7. The computer-implemented method of claim 1, wherein tracking the connected fluid phase region over a series of timeframes comprises:
   identifying a first connected fluid phase region in a first timeframe; and
   identifying a second connected fluid phase region in a second timeframe as being the first connected fluid phase region based on a spatial proximity between the first connected fluid phase region and the second connected fluid phase region.

8. The computer-implemented method of claim 7, wherein the spatial proximity includes an overlap of fluid phase regions between the first connected fluid phase region and the second connected fluid phase region.

9. The computer-implemented method of claim 1, wherein determining the movement of the connected fluid phase region comprises:
   calculating a center of gravity for the connected fluid phase region; and
   determining a velocity for the connected fluid phase region based on the center of gravity.

10. The computer-implemented method of claim 9, wherein determining the velocity of the connected fluid phase region further comprises identifying the change in the center of gravity for the connected fluid phase region between the first timeframe and the second timeframe.

11. The computer-implemented method of claim 1, wherein the connected fluid phase region comprises a series of volume elements, each volume element having the same phase and being in contact with at least one other volume element in the series.

12. The computer-implemented method of claim 1, further comprising:
   identifying a plurality of connected fluid phase regions, each connected fluid phase region having a target phase;
   determining a velocity for each connected fluid phase region in the plurality of connected fluid phase regions; and
   assigning an permeability to the target phase based on the velocity of each connected fluid phase region in the plurality of connected fluid phase regions.

13. The computer-implemented method of claim 12, wherein assigning the permeability to the phase comprises:
   calculating a weighted average of the velocity of each connected fluid phase region having the target phase.

14. The computer-implemented method of claim 13, wherein the velocities are weighted based on the volumes of the connected fluid phase regions.

15. The computer-implemented method of claim 1, further comprising:
   determining properties of the connected fluid phase region in the first timeframe and the second timeframe.

16. The computer-implemented method of claim 15 wherein the properties are selected from the group consisting of: volume, effective permeability, and flow rate.

17. A non-transitory computer storage medium encoded with computer program instructions that when executed by one or more computers cause the one or more computers to perform operations comprising:

identifying a connected fluid phase region in a flow simulation;

tracking the connected fluid phase region over a first timeframe and a second timeframe; and determining movement of the connected fluid phase region from the first timeframe to the second timeframe based on the tracking.

18. The non-transitory computer storage medium of claim 17, wherein identifying the connected fluid phase region comprises:

identifying a fluid phase region having a first phase;

identifying fluid phase regions neighboring the first phase region and having the first phase; and assigning the neighboring fluid phase regions to the connected fluid phase region.

19. The non-transitory computer storage medium of claim 17, wherein the flow simulation comprises a plurality of fluid phase regions; and the method further comprises identifying a phase for each fluid phase region.

20. The non-transitory computer storage medium of claim 17, wherein the connected fluid phase region comprises oil; and the method further comprises determining trapped oil based on the movement.

21. The non-transitory computer storage medium of claim 17, wherein tracking the connected fluid phase region comprises at least one of: identifying that the connected fluid phase region has moved, identifying that the connected fluid phase region has split into multiple connected fluid phase regions, and identifying that the connected fluid phase region has merged with another connected fluid phase region.

22. The non-transitory computer storage medium of claim 17, wherein tracking the connected fluid phase region over a series of timeframes comprises:

identifying a first connected fluid phase region in a first timeframe; and identifying a second connected fluid phase region in a second timeframe as being the first connected fluid phase region based on a spatial proximity between the first connected fluid phase region and the second connected fluid phase region.

23. The non-transitory computer storage medium of claim 22, wherein the spatial proximity includes an overlap of fluid phase regions between the first connected fluid phase region and the second connected fluid phase region.

24. The non-transitory computer storage medium of claim 17, wherein determining the movement of the connected fluid phase region comprises:

calculating a center of gravity for the connected fluid phase region; and determining a velocity for the connected fluid phase region based on the center of gravity.

25. The non-transitory computer storage medium of claim 17, wherein the connected fluid phase region comprises a series of volume elements, each volume element having the same phase and being in contact with at least one other volume element in the series.

26. The non-transitory computer storage medium of claim 17, further comprising:

identifying a plurality of connected fluid phase regions, each connected fluid phase region having a target phase;

determining a velocity for each connected fluid phase region in the plurality of connected fluid phase regions; and assigning an permeability to the target phase based on the velocity of each connected fluid phase region in the plurality of connected fluid phase regions.

27. The non-transitory computer storage medium of claim 1, further comprising:

determining properties of the connected fluid phase region in the first timeframe and the second timeframe.

28. A system comprising:

one or more computers and one or more storage devices storing instructions that are operable, when executed by the one or more computers, to cause the one or more computers to perform operations comprising:

identifying a connected fluid phase region in a flow simulation;

tracking the connected fluid phase region over a first timeframe and a second timeframe; and determining movement of the connected fluid phase region from the first timeframe to the second timeframe based on the tracking.

29. The system of claim 28, wherein identifying the connected fluid phase region comprises:

identifying a fluid phase region having a first phase;

identifying fluid phase regions neighboring the first phase region and having the first phase; and assigning the neighboring fluid phase regions to the connected fluid phase region.

30. The system of claim 28, wherein tracking the connected fluid phase region over a series of timeframes comprises:

identifying a first connected fluid phase region in a first timeframe; and identifying a second connected fluid phase region in a second timeframe as being the first connected fluid phase region based on a spatial proximity between the first connected fluid phase region and the second connected fluid phase region.

* * * * *

UNITED STATES PATENT AND TRADEMARK OFFICE
CERTIFICATE OF CORRECTION

PATENT NO. : 9,228,873 B2
APPLICATION NO. : 14/660019
DATED : January 5, 2016
INVENTOR(S) : Bernd Crouse, David M. Freed and Nils Koliha It is certified that error appears in the above-identified patent and that said Letters Patent is hereby corrected as shown below:

On the title page, item (56) under OTHER PUBLICATIONS, Col. 2, line 2, delete "prorous" and insert -- porous --, therefor.

Signed and Sealed this
Twenty-eighth Day of June, 2016

Michelle K. Lee
*Director of the United States Patent and Trademark Office*